(12) United States Patent
Sung et al.

(10) Patent No.: US 8,618,057 B2
(45) Date of Patent: Dec. 31, 2013

(54) ANTICOAGULANT AND COMPOSITION FOR PREVENTING THROMBUS CONTAINING POLY-GAMMA-GLUTAMIC ACID

(75) Inventors: Moon-Hee Sung, Daejeon (KR); Chung Park, Daejeon (KR); Seung-Pyo Hong, Daejeon (KR); Haryoung Poo, Daejeon (KR); Tae-Woo Kim, Gyeonggi-do (KR)

(73) Assignee: Bioleaders Corporation, Daejeon (KR)

( * ) Notice: Subject to any disclaimer, the term of this patent is extended or adjusted under 35 U.S.C. 154(b) by 0 days.

(21) Appl. No.: 13/444,324

(22) Filed: Apr. 11, 2012

(65) Prior Publication Data

US 2012/0196806 A1  Aug. 2, 2012

Related U.S. Application Data

(62) Division of application No. 12/159,561, filed as application No. PCT/KR2006/005685 on Dec. 22, 2006, now abandoned.

(30) Foreign Application Priority Data

Dec. 29, 2005  (KR) .................. 10-2005-0133055

(51) Int. Cl.
*A61K 38/02* (2006.01)
(52) U.S. Cl.
USPC ..................................... 514/13.7; 514/21.2
(58) Field of Classification Search
None
See application file for complete search history.

(56) References Cited

U.S. PATENT DOCUMENTS

| | | | |
|---|---|---|---|
| 2003/0228347 A1 | 12/2003 | Clark et al. | |
| 2009/0186804 A1 | 7/2009 | Sung et al. | |

FOREIGN PATENT DOCUMENTS

| | | |
|---|---|---|
| EP | 0838160 A1 | 4/1998 |
| JP | 5117388 | 5/1993 |
| JP | 6032742 | 2/1994 |
| JP | 6092870 | 4/1994 |
| JP | 6256220 | 9/1994 |
| JP | 7138364 | 5/1995 |
| KR | 1020020079889 A | 10/2002 |
| KR | 100475406 B1 | 2/2005 |
| KR | 100496606 B1 | 6/2005 |
| KR | 100517114 B1 | 9/2005 |
| WO | 2004007593 A1 | 1/2004 |

OTHER PUBLICATIONS

Matsusaki et al. ("Novel Functional Biodegradable Polymer: Synthesis and Anticoagulant Activity of Poly(_-Glutamic Acid)sulfonate (_-PGA-sulfonate)," Bioconjugate Chem. 2002, 13, 23-28).*
Kraut, Joseph, "Serine Proteases: Structure and Mechanism of Catalysis," Ann. Rev. Biochem., 46: 331-358 (1977) (abstract).

(Continued)

*Primary Examiner* — Christina Bradley
(74) *Attorney, Agent, or Firm* — Tristan A. Fuierer; Moore & Van Alllen, PLLC

(57) ABSTRACT

The present invention relates to an anticoagulant and a composition for preventing thrombus formation, which contain poly-gamma-glutamic acid (PGA) as an active ingredient. The inventive PGA is a water-soluble, anionic, biodegradable and edible amino acid polymer material, which has an anticoagulant effect of preventing thrombi from being accumulated in blood vessels, shows an excellent sustained-release effect and is harmless to the human body. Thus, it is useful as a high-value-added anticoagulant and a food or beverage composition for preventing thrombus formation.

4 Claims, 2 Drawing Sheets

(56) References Cited

OTHER PUBLICATIONS

Harlan, John M., et al., "Hemostasis, Thrombosis, and Thromboembolic Disorders," Med. Clin. North America, 65:855-880 (1981).

Mutlu, Nusret, et al., "Massive Cerebral Hemorrhage," Arch. Neurol., 8:644-661 (1963).

Mullertz, S., "International Committee for Fibrinolysis? Kabi Prize Lecture 1986. Fibrinolysis, General aspects characteristic features and prespectives," Fibrinolysis, 1:3-12 (Jan. 1987) (abstract).

Craik, CS, et al., "The catalytic role of the active site aspartic acid in serine protease," Science, 237 (4817): 909-913 (Aug. 21, 1987) (abstract).

Gomez Calvino, Carmen, et al., "Relacion entre la peroxidacion lipidica y agregacion plaquetaria en pacientes ateroscleroticos," Angiologia, 43: 241-246, (1991).

Mihara, Hisashi, et al., "A Novel Fibrinolytic Enzyme Extracted from the Earthworm, *Lumbricus rubellus*," Japanese Journal of Physiology, 41: 461-472 (1991).

Dake, Michael D., et al., "Thrombolytic Therapy in Venous Occlusive Disease," Journal of Vascular and Interventional Radiology, 6:73-77 (1995).

Ito, Yoshihito, et al., "Glutamic Acid Independent Production of Poly(y-glutamic acid) by *Bacillus subtillis* TAM-4," Biosci, Biotech. Biochem., 60(8): 1239-1242 (1996).

* cited by examiner

US 8,618,057 B2

ANTICOAGULANT AND COMPOSITION FOR PREVENTING THROMBUS CONTAINING POLY-GAMMA-GLUTAMIC ACID

CROSS-REFERENCE TO RELATED APPLICATIONS

This application is a divisional application of and claims the priority of U.S. patent application Ser. No. 12/159,561 filed on Jun. 27, 2008 entitled "Anticoagulant and Composition for Preventing Thrombus Containing Poly-Gamma-Glutamic Acid" in the name of Moon-Hee SUNG, et al., which claims priority of International Patent Application No. PCT/KR2006/005685 filed on Dec. 22, 2006, which claims priority of Korean Patent Application No. 10-2005-0133055, filed Dec. 29, 2005, all of which are hereby incorporated by reference herein in their entireties.

TECHNICAL FIELD

The present invention relates to an anticoagulant and a composition for preventing thrombus formation, which contain poly-gamma-glutamic acid (PGA) as an active ingredient.

BACKGROUND ART

Blood coagulation is a cascade of hemostatic events during which blood changes from a liquid state to a gel state. Hemostatic events in the body occur only around injured blood vessels, and are elaborately regulated by selective binding between various coagulation factors, proteolysis inhibitors present in plasma, and a series of antagonistic enzyme reactions (Harlan, J. M. et al., Med. Clin. North Am., 65:855, 1981). Despite this elaborate regulation, when the balance between blood coagulation and lysis is broken due to various abnormal or external factors, excessive thrombus formation will occur, resulting in cerebral apoplexy, heart failure and the like (Gormez, C. C. et al., Angiologia, 43:241, 1991).

Cerebral apoplexy is a cerebral nerve disorder, including consciousness disorder and movement disorder, caused by various cerebrovascular diseases, and is a serious disease which is the first leading cause fod death in both men and women in Korea. It is impossible to regenerate tissue necrosis caused by cerebral apoplexy. Thus, to treat the root cause of the disease, risk factors should be removed, treatment for regenerable tissue and the facilitation of regeneration should be conducted first, and mental treatment and physical treatment are also required, because tissue necrosis can be followed by cerebral injury and neurological complications resulting from an increase in cerebral pressure. Methods for treating cerebral apoplexy include providing sufficient blood flow to ischemic areas and using drug therapies, including anticoagulants, anti-platelet agents, thrombolytic agents, blood viscosity-reducing agents, and agent for stopping the progression of ischemia, which protect cells in ischemic changes.

Typical causes of cerebral apoplexy include diseases, such as hypertension, hyperlipidemia, heart disease, thrombosis and diabetes, oral contraceptives, smoking, alcohol drinking and the like. Among these causes, hypertension is the most risky factor that must be treated first (Matlu, N. et al., Arch. Neural., 8:644, 1963), and when problems associated with cerebral apoplexy occur, calcium antagonists such as dihydropyridine and angiotensin conversion enzyme inhibitors are used. Hyperlipidemia causes arteriosclerosis, and thus is treated using diet therapy together with niacin having the effect of suppressing lipolysis, clofibrate and gemfibrozil of having the effect activating lipoprotein lipase to lower tracylglycerol levels, resins binding to bile acid, cholestyramine and colestipol, lovastatin and pravastatin having the effect of suppressing enzyme HMG-CoA reductase to inhibit cholesterol synthesis, and the like.

Meanwhile, anticoagulants are drugs for preventing blood coagulation (thrombosis) caused by either foreign matter (artificial valve) in the cardiovascular system or arrhythmia. Anticoagulant therapy is used for the treatment and prevention of deep vein thrombosis, pulmonary embolism, heart diseases, cerebral embolism, etc., and after artificial heart valve replacement. Typical drugs that are used in such anticoagulant therapy include heparin, a kind of acidic polysaccharide having sulfate groups, which is a strong inhibitor of blood coagulation, and vitamin K antagonist warfarin. In addition, fraxiparine, enoxaparin, etc., are also used. Heparin binds to antithrombin III to show a rapid anticoagulant effect. Antithrombin III is also called heparin coenzyme and inhibits various coagulation factors such as serine protease and thrombin. Because an overdose of heparin reduces rather than increases the activity of antithrombin, thus resulting in the risk of thrombosis, low-dose heparin is used through intravenous injection or subcutaneous injection, and the dose thereof is determined while the degree of blood coagulation in a patient is checked whenever needed.

Vitamin K antagonists include warfarin and dicumarol. Warfarin is an oral anticoagulant showing the effect of inhibiting coagulant factors in the body, and is used in long-term anticoagulant therapy. Warfarin acts instead of vitamin K, a coenzyme involved in the synthesis of proteins involved in blood coagulation, so as to inactivate coagulant factors. Because the inactivation of coagulation factors takes long time, warfarin is not used in acute situations.

Anticoagulants are replaced with other methods about 3 months after the use in cases other than diseases where thrombi are formed. Heparin, a mucopolysaccharide having an anticoagulant effect, is distributed in internal organs having many capillary blood vessels (e.g., liver, lungs, kidneys and muscles) or blood in the higher animals. It is present as a mucoprotein in animal tissues and is purified by extracting it with alkali and removing a protein with an enzyme. It has a molecular weight of about 10,000-20,000 and possesses a structure in which D-glucosamine, D-glucuronic acid and L-iduronic acid are chemically bonded in a chain configuration. It prevents the production of thromboplastin, increases the rate of binding of antithrombin to thrombin to inhibit blood coagulation, and furthermore, purifies blood by inducing and synthesizing lipase that degrades serum lipoproteins. Heparin is a main drug, which is used against venous thrombosis and pulmonary embolism, and reduces the number of thrombosis, stroke. Moreover, it is also used for the prevention of venous thrombosis and acute myocardial infraction after surgical operations. Although it does not pass through the placenta, special attention must be paid to the use thereof in pregnant women.

Meanwhile, fibrinogen is hexaprotein, a kind of water-soluble plasma protein, which has a molecular weight of 340 kDa, is present at a concentration of about 2.5 mg/mL in the body, and is converted into fibrin by thrombin (Craik, C. S. et al., Science, 237:909, 1987). The fibrin thus produced plays an important role in blood coagulation and is a fundamental substance for thrombus formation. Plasmin performs various roles, including the degradation of coagulated fibrin in the body, the inhibition of 2-antiplasmin, the regeneration of injured tissues, and the activation of macrophages (Daka, M. D. et al., J. Vasc. Intern. Radiol., 6:73, 1995). Plasmin is generally present in the form of a zymogen, called plasminogen, and will change into an activated form to show fibrinolytic activity when $Arg^{561}$-$Val^{562}$ is degraded by a plasminogen activator (Mullertz, S., *Fibrinolysis*, 1:3, 1987). This fibrinolytic system has a function of protecting the body from thrombus formation, which is a kind of defense function against the deposition of fibrin in blood vessels. Enzymes having this fibrinolytic activity are mostly serine proteases such as plasmin, and microorganisms such as *Bacillus subtilis* produce various kinds of serine proteases (Kraut, J., *Ann. Rev. Biochem.*, 46:331, 1977).

Therapeutic agents, which have been used to date for the treatment of thrombosis, include streptokinase, urokinase, tissue-type plasminogen activators (tPA) and the like, but such therapeutic agents employing serine proteases have problems in that they are uneconomical, have a short half life, show side effects such as blood vessel bleeding upon misuse, and are difficult to administer orally, except for urokinase. Recently, the medical college team at Miyazaki University, Japan, has made an oral therapeutic agent by isolating six lumbrikinases from earthworms which have been used for the treatment of palsy, but this product also problems in that it has a short half life and is expensive (Mihara, H. et al., *Lubricus rubellus Jan. J. Physiol.*, 41:461, 1991).

Meanwhile, PGA is a viscous liquid polymer consisting of D,L-glutamic acid bound to γ-glutamyl, and is a natural, edible, water-soluble, anionic, biodegradable polymeric substance, which is produced from *Bacillus* sp. strains isolated from Chungkookjang (Korean traditional fermented soybean food prepared using rice-straw), Natto (Japanese traditional fermented soybean food) and Kinema (Nepalese traditional fermented soybean food), and can be used as a moisture absorber, a moisturizer and a raw material for cosmetics.

Recently, with respect to the production and utilization of PGA, studies focused on the material of products substituting for non-biodegradable polymers, the development of heat-resistant plastics by esterification and the production of water-soluble fibers and membranes have been actively conducted in, particularly, advanced countries. Also, studies focused on developing and industrializing environment-friendly material, hydrogel having water absorptivity, biodegradability and plasticity, using PGA as a raw material, have been conducted. In such studies, when an aqueous solution containing PGA is treated with a chemical crosslinking agent and irradiated with radiation, the crosslinking reaction between the molecules of PGA can occur to provide PGA resin having water absorptivity, biodegradability and plasticity. Such PGA resin is a polymeric substance, which is highly applicable in hygienic products such as diapers, food, horticultural industries.

Moreover, the following studies and patents, for example, have been reported: the effects of manganese ions on the composition and production of PGA, the use of PGA as water-soluble polymers by untrasonic decomposition, and the development of low-water-soluble plastics by the synthesis of ester derivatives (Ito, Y. et al., *Biosci. Biotechnol. Biochem.*, 60:1239, 1996); the production of PGA by *Bacillus subtillis*, and the use of PGA as a calcium dissolving agent in healthy foods having an osteoporosis therapeutic effect (JP 6-32742); effects of reducing the content of phosphorus in water systems to reduce water contamination (EP 838160); the use of PGA as biodegradable solid fibers or films and molded films by the dissolution, precipitation and drying of PGA (JP 7-138364 and JP 5-117388); and polymers for drug carriers (JP 6-92870 and JP 6-256220). Thus, PGA is a highly useful natural polymer, which can be used as low-water-soluble plastics, healthy foods having osteoporosis therapeutic effects, agents for reducing water contamination, biodegradable fibers or films and molded films, polymers for drug carriers, and the like.

The present inventors acquired a patent (Korean Patent Registration No. 10-500796) relating to a method of producing poly-gamma-glutamic acid (PGA) using *Bacillus subtilis* chungkookjang, a halotolerant strain producing high-molecular-weight PGA, and furthermore, acquired patents relating to an anticancer composition containing PGA, an immune adjuvant and an immune booster (Korean Patent Registration Nos. 10-496606; 10-517114; and 10-475406). However, there is still no report on the effects of PGA on anticoagulation and/or thrombus prevention.

Accordingly, the present inventors have made extensive efforts to elucidate the various functions of PGA having various applications and, as a result, found that PGA, which is inexpensive and non-toxic to the human body, has an anticoagulant effect of preventing blood coagulation (thrombosis) caused by arrhythmia, and thus it can prevent thrombi from being accumulated and has excellent water absorption, sustained release, thermal stability, and nontoxic properties to cells, thereby completing the present invention.

SUMMARY OF THE INVENTION

Therefore, it is a main object of the present invention to provide an anticoagulant containing poly-gamma-glutamic acid (PGA) as an active ingredient.

Another object of the present invention is to provide a food or beverage composition for preventing thrombus formation, which contains PGA as an active ingredient.

To achieve the above objects, the present invention provides an anticoagulant containing PGA as an active ingredient.

Furthermore, the present invention provides a pharmaceutical composition for preventing thrombus formation, which contains PGA as an active ingredient.

In addition, the present invention provides a food for preventing thrombus formation, which contains PGA as an active ingredient.

The other features and embodiments of the present invention will be more clearly understood from the following detailed description and the accompanying claims

DETAILED DESCRIPTION OF THE INVENTION, AND PREFERRED EMBODIMENTS

Figure 1:
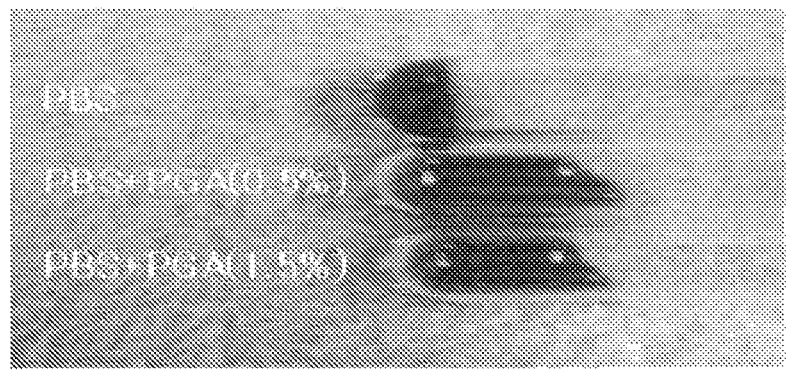
FIG. 1 is a photograph showing the anticoagulant effect of PGA.

The present invention relates to an anticoagulant and a composition for preventing thrombus formation, which contain PGA as an active ingredient.

The PGA of the present invention is a water-soluble, anionic, biodegradable and edible amino acid polymer material, which has an anticoagulant effect of preventing thrombi from being accumulated in blood vessels, has excellent water absorption and sustained release properties, and is harmless to the human body. Accordingly, the inventive anticoagulant containing PGA as an active ingredient can be administered orally or parenterally, can be prepared for pharmaceutical use according to a method known in the pharmaceutical field, and can be formulated into, for example, tablet, capsules, powders, liquids, suspensions and injection solutions, using suitable excipients.

In the present invention, PGA having molecular weights of 50 kDa, 2,000 kDa, 4,000 kDa and 10,000 kDa all showed high anticoagulant effects, and had similar anticoagulant effects at these concentrations, and thus it was found that PGA had a high anticoagulant effect regardless of the molecular weight thereof in a molecular weight range of 50-10,000 kDa. Accordingly, the molecular weight of PGA is preferably 1-15,000 kDa.

PGA, which is used in the present invention, may be one produced by chemical synthesis or microbial fermentation, preferably one produced by microbial fermentation, and more preferably one produced by the fermentation of *Bacillus subtilis* chungkookjang.

The composition for preventing thrombus formation according to the present invention is preferably a food composition. The PGA of the present invention has little or no side effects and toxicity, so that it can be used for preventative purposes without fear even in long-term administration, and thus can be used as a main component or an additive or adjuvant for preparing food for the prevention of thrombus formation.

The food for preventing thrombus formation according to the present invention, which contains PGA, may preferably contain the inventive PGA in an amount of 0.01-100 wt %, and more preferably 0.01-5 wt % for beverages, even though the content of the poly-gamma glutamic acid varies depending on a food group to which it is added.

The food for preventing thrombus formation according to the present invention may be a food for preventing thrombus formation, which contains the inventive PGA and is prepared using green tea, *Ganoderma lucidum*, black tea, *Polygonatum odoratum*, lemon, ginseng, jujube, ginkgo leaves, *Coriolus versicolor*, *Pisolithus tinctorius*, *Tricholomopsis decora* and/or *Cordyceps militaris*, but any food can be used in the present invention without limitation, as long as it contains the inventive poly-gamma-gultamic acid as an active ingredient, and thus can provide an anticoagulant effect.

EXAMPLE

The present invention will hereinafter be described in further detail by examples. However, it is to be understood that these examples can be modified into other various forms, and the scope of the present invention is not intended to be limited to such examples. Such examples are given to more fully describe the present invention for a person skilled in the art.

Example 1

Preparation of PGA

PGA was prepared according to the method described in the previous patent (WO 04/007593) filed in the name of the present inventors. That is, culture broth of *Bacillus subtilis var chungkookjang* (KCTC 0697BP) was inoculated into a fermentor containing a basal medium to provide a PGA-containing sample solution. Then, the sample solution was left to stand to remove polysaccharides from the fermented solution, and the PGA precipitate was added with distilled water to dissolve. Next, protease was added to the solution and left to stand in incubator to degrade extracellular proteins present in the PGA sample, followed by dialyzing in a sufficient amount of distilled water to remove free glutamic acid, and concentrating to provide pure PGA. From which it could be seen that the PGA thus obtained had an average molecular weight of 13,000 kDa, more than 95% of the PGA molecules had a molecular weight ranging from 3,000 to 15,000 kDa, and the PGA had a molecular weight distribution ranging from 1 kDa to 15,000 kDa.

Example 2

Anticoagulant Effect of PGA

Blood was collected from C57BL/6 mice and then mixed with the PGA solution prepared in Example 1, at a ratio of 1:1. The blood sample was left to stand at room temperature for about 20 minutes, and FACS (Fellow of the American College of Surgeons) tubes containing the blood samples at varying concentrations were laid at an angle of 90° to compare blood fluidity between the blood samples, thus determining the degree of coagulation of the blood samples. As a result, the PGA had an anticoagulant ability at a concentration of 0.5% (see FIG. 1).

Example 3

Anticoagulant Effect According to Molecular Weight of PGA

Figure 2:
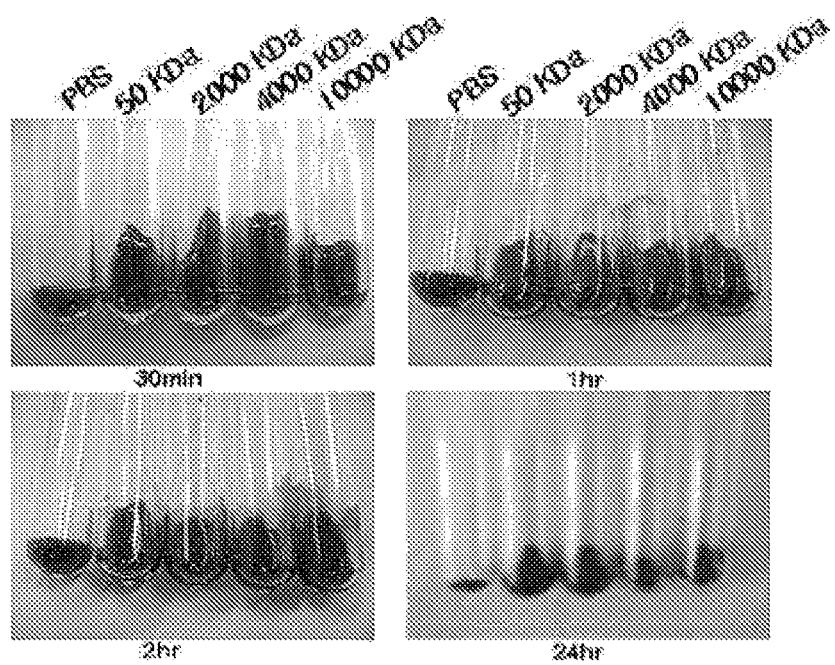
FIG. 2 is a photograph showing the anticoagulant effect of PGA according to the molecular weight thereof.

Blood was collected from C57BL/6 mice and then mixed with the 0.5% PGA-containing solution prepared in Example 1, at a ratio of 1:1. The blood sample was left to stand at room temperature, and FACS tubes containing the blood were laid at an angle of 90° to compare blood fluidity between the blood samples, thus determining the degree of coagulation of the blood samples. As a result, the PGA showed similar anticoagulant effects at molecular weights of 50 kDa, 2,000 kDa, 4,000 kDa and 10,000 kDa. Thus, it could be found that the PGA showed similar anticoagulant effects in a molecular weight range of 50-10,000 kDa regardless of the molecular weight thereof (see FIG. 2).

Example 4

Comparison of Anticoagulant Effects of PGA

Figure 3:
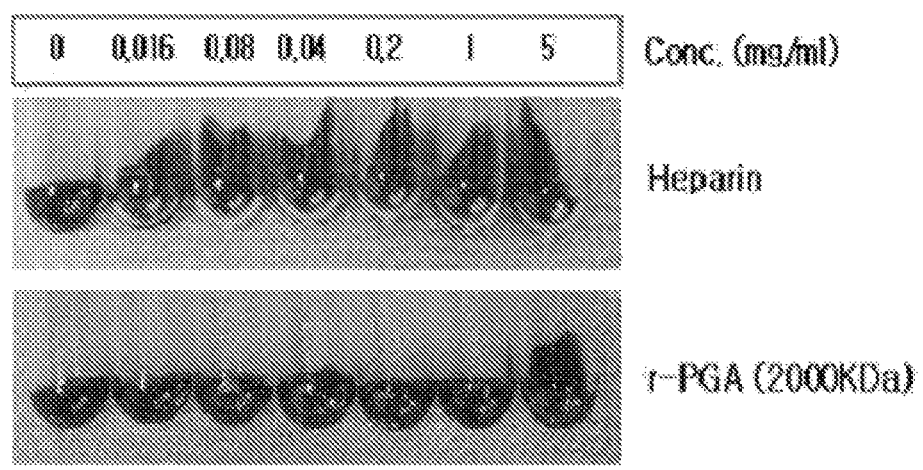
FIG. 3 is a photograph showing the anticoagulant effect of PGA compared to a heparin solution.

Blood was collected from C57BL/6 mice, and then the PGA-containing solution prepared in Example 1, and a heparin solution were added to the blood at varying concentrations. The blood samples were left to stand at room temperature for about 20 minutes, and FACS tubes containing the blood samples were laid at an angle of 90° to compare blood fluidity between the blood samples, thus determining the degree of coagulation of the blood samples. As a result, it was seen that the PGA had an anticoagulant ability similar to heparin at a concentration of 5 mg/mL (see FIG. 3).

Hereinafter, green tea and brown rice green tea will be illustrated as PGA-containing foods for the prevention of thrombus formation in the following formulation examples, but formulations containing the inventive food and beverage composition are not limited thereto.

Formulation Example 1

Preparation of Green Tea Containing PGA

Harvested green tea leaves were collected, and steamed tea manufactured using the collected tea leaves according to a standard process for manufacturing steamed tea was used as a raw material. The green tea leaves were milled in a mill to a size of about 1.0-3.0 mm to obtain green tea powder. The PGA powder prepared in Example 1 and the green tea powder were mixed at a ratio of 0.2:9.8 to 0.3:9.7 (on dry weight basis) and used as canned beverage. The green tea powder and the PGA were well mixed with each other in a mixer to obtain thrombus-preventing green tea for use as tea bag products.

Formulation Example 2

Preparation of PGA-Containing Brown Rice Green Tea

The thrombus-preventing green tea obtained in the present invention, when used as powder for tea bag products, may contain brown rice for improving preference in order to reduce a puckery taste and to harmonize entire fragrance. For this purpose, carefully selected brown rice was washed with water and then steamed at 100° C. for 30-60 minutes to make steamed rice. Then, the steamed rice was pretreated according to a conventional steaming process comprising, for example spreading the steamed rice on a drying sheet and drying the spread steamed rice in hot air at 80° C. for about 3-4 hours, and the pretreated brown rice was roasted in an iron pot at a temperature of 100-180° C. until it turned light yellow, such that it was not burnt. Then, the roasted brown rice was milled in a mill to a size of 1.0-3.0 mm to provide brown rice powder for use as a tea bag product.

The thrombus-preventing green tea prepared in Formulation Example 1 and the brown rice powder were mixed with each other at a ratio of 2:1 to 4:1, and powdery perfume was added thereto in an amount of 0.02-0.06% (w/w %). The mixture was well mixed in a mixer for 30-40 minutes, thus obtaining a thrombus-preventing brown rice green tea for use as tea bag products.

INDUSTRIAL APPLICABILITY

As described and proven in detail above, the prevent invention provides the anticoagulant and the composition for preventing thrombus formation, which contain PGA as an active ingredient. The inventive composition containing PGA is inexpensive, has a long half life, shows an excellent anticoagulant effect, and has little or no toxicity and side effects, and thus can be administered for preventative purposes for a long period of time. Also, it is useful for the development of foods and beverages for preventing thrombus formation, and thus can prevent or mitigate cerebral apoplexy, myocardial infraction, thrombosis and the like through food intake. Accordingly, the long-term intake of the PGA-containing food will be useful for the treatment and prevention of various vascular diseases.

While the present invention has been described with reference to the particular illustrative embodiment, it is not to be restricted by the embodiment but only by the appended claims. It is to be appreciated that those skilled in the art can change or modify the embodiment without departing from the scope and spirit of the present invention.

What is claimed is:

1. A method of inhibiting blood coagulation comprising administering to a patient in need thereof an anticoagulant comprising a therapeutically effective amount of poly-gamma-glutamic acid (PGA) as an active ingredient.

2. The method accord to claim 1, wherein the molecular weight of said poly-gamma-glutamic acid (PGA) is 1-15,000 kDa.

3. A method of preventing thrombus formation comprising administering to a patient in need thereof a pharmaceutical composition comprising a therapeutically effective amount of poly-gamma-glutamic acid (PGA) as an active ingredient.

4. The method according to claim 3, wherein the molecular weight of said poly-gamma-glutamic acid is 1-15,000 kDa.

* * * * *